United States Patent
Hoornaert et al.

(10) Patent No.: US 11,253,219 B2
(45) Date of Patent: Feb. 22, 2022

(54) IMAGE CONTRAST ENHANCEMENT OF AN X-RAY IMAGE

(71) Applicant: KONINKLIJKE PHILIPS N.V., Eindhoven (NL)

(72) Inventors: Bart Pierre Antoine Jozef Hoornaert, Arendonk (BE); Raoul Florent, Ville D'Avray (FR); Claire Levrier, Rueil-Malmaison (FR); Bernardus Marius Hubertus Gevers, Sint Oedenrode (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/623,198

(22) PCT Filed: Jun. 26, 2018

(86) PCT No.: PCT/EP2018/067005
§ 371 (c)(1),
(2) Date: Dec. 16, 2019

(87) PCT Pub. No.: WO2019/002230
PCT Pub. Date: Jan. 3, 2019

(65) Prior Publication Data
US 2021/0145391 A1  May 20, 2021

(30) Foreign Application Priority Data

Jun. 29, 2017 (EP) .................................... 17305821

(51) Int. Cl.
*A61B 6/00* (2006.01)
*G16H 30/40* (2018.01)
*G06T 5/00* (2006.01)

(52) U.S. Cl.
CPC ............ *A61B 6/5205* (2013.01); *G06T 5/007* (2013.01); *G16H 30/40* (2018.01); *G06T 2207/10116* (2013.01); *G06T 2207/30101* (2013.01)

(58) Field of Classification Search
None
See application file for complete search history.

(56) References Cited

U.S. PATENT DOCUMENTS 5,461,655 A  10/1995 Vuylsteke et al.
7,821,266 B2 10/2010 Feiweier
(Continued)

FOREIGN PATENT DOCUMENTS

WO  WO-03039601 A1 * 5/2003 ................ A61P 9/08
WO  2007059602 A1  5/2007

OTHER PUBLICATIONS

Schaetzing: "AGFA'S MUSICA2 Taking Image Processing To the Next Level"; AFGA Healthcare, White Paper, Apr. 2007, 31 Page Document.
(Continued)

*Primary Examiner* — Vu Le
*Assistant Examiner* — Courtney Joan Nelson

(57) ABSTRACT

The present invention relates to image contrast enhancement. In order to provide improved and stable contrast enhancement for each acquired image, a device (10) for image contrast enhancement of an X-ray image of a vascular structure is provided. The device (10) comprises an input unit (12) and a processing unit (14). The input unit is configured to provide an acquired X-ray image of a vascular structure with a contrast injection. The contrast injection is performed with a current contrast injection setting having at least one contrast injection parameter. The input unit is further configured to provide a generic vascular structure. The input unit is also configured to provide the current
(Continued)

contrast injection setting. The processing unit is configured to determine an assessed contrast parameter for the generic vascular structure based on the current contrast injection setting. The processing unit is further configured to determine an adapted image contrast enhancement for the generic vascular structure based on the assessed contrast parameter. The processing unit is also configured to apply the adapted image contrast enhancement to the acquired X-ray image in order to generate a contrast-enhanced X-ray image.

18 Claims, 2 Drawing Sheets

(56) References Cited

U.S. PATENT DOCUMENTS

| | | | |
|---|---|---|---|
| 9,008,759 B2 | 4/2015 | Kalafut et al. | |
| 2005/0228273 A1* | 10/2005 | Tamakoshi | A61B 6/548 600/425 |
| 2008/0253634 A1 | 10/2008 | Hay et al. | |
| 2012/0229504 A1* | 9/2012 | Nakamura | A61B 6/481 345/629 |
| 2016/0135770 A1* | 5/2016 | Eshuis | A61B 6/485 600/431 |
| 2017/0018081 A1* | 1/2017 | Taylor | A61B 6/5217 |

OTHER PUBLICATIONS

PC/EP/2018/067005 ISR & WO, dated Oct. 17, 2019, 14 Page Document.

Stahl et al.: "Digital Radiography Enhancement By Nonlinear Multiscale Processing"; Med. Phys. 27 (1), Jan. 2000, pp. 56-65.

Vuylsteke et al.: "Multiscale Image Contrast Amplification (Musica)"; Event Imaging 1994: Image Processing, (May 11, 1994), pp. 551-560.

Vuylsteke et al.: "Image Processing in Computed Radiography"; DGZfP Proceedings BB 676-CD Paper 16, pp. 87-101.

* cited by examiner

IMAGE CONTRAST ENHANCEMENT OF AN X-RAY IMAGE

CROSS-REFERENCE TO PRIOR APPLICATIONS

This application is the U.S. National Phase application under 35 U.S.C. § 371 of International Application No. PCT/EP2018/067005, filed on Jun. 26, 2018, which claims the benefit of European Patent Application No. 17305821.5, filed on Jun. 29, 2017. These applications are hereby incorporated by reference herein.

FIELD OF THE INVENTION

The present invention relates to a device for image contrast enhancement of an X-ray image of a vascular structure, to a system with a such device, to a method for image contrast enhancement of an X-ray image of a vascular structure, to a computer program element for controlling such a device and to a computer readable medium having stored the program element.

BACKGROUND OF THE INVENTION

In X-ray images, contrast enhancement (CE) is provided to improve image quality for the viewer. Contrast enhancement may be realized in the framework of frequency decomposition. For example, the image is decomposed into a certain number of frequency sub-bands, for instance, with a so-called Laplacian Pyramid. The anatomical or interventional details one is willing to enhance are spread across several of those frequency sub-bands. Gains, which may depend on the local intensity are then applied to the content of those sub-bands, before the total spectrum is re-composed, thus leading to an enhancement. In order to achieve an improved image quality, and thus better image contrast with satisfactory signal-to-noise ratio, in U.S. Pat. No. 7,821,266 B2, a simulation image is calculated and the operator can virtually optimize the imaging parameters online and modify them. In U.S. Pat. No. 9,008,759 B2, a model descriptive of propagation of a fluid within a patient is provided and parameters for the injection procedure are determined to generate desired levels of enhancement. However, it has been shown that contrast enhancement is still not always leading to sufficient results.

SUMMARY OF THE INVENTION

There may thus be a need to provide improved and stable contrast enhancement for each acquired image.

The object of the present invention is solved by the subject-matter of the independent claims; further embodiments are incorporated in the dependent claims. It should be noted that the following described aspects of the invention apply also for the device for image contrast enhancement of an X-ray image of a vascular structure, for the system with a such device, for the method for image contrast enhancement of an X-ray image of a vascular structure, and for the computer program element for controlling such a device and also for the computer readable medium having stored the program element.

According to a first aspect, a device is provided for image contrast enhancement of an X-ray image of a vascular structure. The device comprises an input unit and a processing unit. The input unit is configured to provide an acquired X-ray image of a vascular structure with a contrast injection. The contrast injection is performed with a current contrast injection setting having at least one contrast injection parameter. The input unit is configured to provide a generic vascular structure. The input unit is configured to provide the current contrast injection setting. The processing unit is configured to determine an assessed contrast distribution for the generic vascular structure based on the current contrast injection setting. The processing unit is configured to determine an adapted image contrast enhancement for the generic vascular structure based on the assessed contrast distribution. The processing unit is also configured to apply the adapted image contrast enhancement to the acquired X-ray image in order to generate a contrast-enhanced X-ray image.

In an example, the current injection setting is read-in in the processing unit.

In an example, the generic vascular structure is read-in in the processing unit.

In an example, the generic vascular structure is provided at least for the targeted vascular structure for which an image is to be captured.

The term "acquired" can also be referred to as captured.

The term "contrast injection" can also be referred to as delivery or supply of a contrast agent, for example with a device which transmits the contrast dilution into an object.

The term "generic vascular structure" can also be referred to as a theoretical model of the human's vessels.

The term "assessed contrast distribution" can also be referred to as an estimation of the distribution of the contrast dilution agent or as the estimated contrast arrangement, or estimated contrast distribution (relating for example to the contrast agent distribution) of the image for the generic vascular structure depending on the current injection setting.

The adapted image contrast enhancement could also be referred to as a contrast value for improving the image quality or boosting or tuning. The adapted image contrast enhancement can also be referred to as predicted contrast enhancement, or predicted adapted contrast enhancement.

In an example, the processing unit is also configured to determine if the assessed contrast distribution is below, equal or above a predetermined threshold.

In an example, the processing unit performs an algorithm for determining adapted image contrast enhancement for the generic vascular structure based on the assessed contrast distribution.

In an example, the adapted contrast image enhancement can be applied by a contrast enhancement procedure or program operating on the processing unit.

In an example, the input unit, or input interface, reads-in the current contrast injection setting.

In an example, when the volume of the iodine concentration is preferably reduced (e.g. because of patient's kidney disease), and hence, a respective adapted contrast injection setting is applied. This assessed contrast distribution for the generic vascular structure is to be predicted to be below or at least different of another value, which can be defined by the determination of the assessed contrast distribution. Based on this information, one can deduce the contrast of vessels to be captured by X-ray prior to vessel boosting or contrast enhancement.

Therefore, the adapted contrast enhancements relies on information to improve the image quality based on the current injection setting. In other words, the adapted image contrast enhancement is a dynamic boosting of images (e.g. the applied contrast enhancement procedure is determined by the current injection settings which is in turn depending on the patient specifics (e.g. kidney disease)). With regards to the above-mentioned example of a patient with kidney disease, the iodine concentration may need to be lowered compared to other patients without this disease. The boosting of the to be captured image of the vessels of the patient can be adapted by considering this adaptation of this injection parameter.

In an example, the adapted image contrast enhancement for the generic vascular structure based on the assessed contrast distribution is performed by an enhancement algorithm. For example, the assessed contrast distribution of the main vessels is used to scale look-up-tables and gains that are applied on the content of the relevant frequency sub-bands of the current X-ray image. In an example, for a typical patient at a typical geometry, the vessel contrast in the image, obtained with a typical (high) iodine concentration, can be postulated to be the desired or reference contrast, or the so-called threshold. It would have a reference value for a Contrast Enhancement parameter. In other situations, for example due to the usage of a strongly diluted iodine concentration (for example: half the concentration), the vessel contrast in the image will be less (for example: half the contrast). Hence the vessels are not only less visible, also the interventionalist or physician misses an absolute reference level. The predicted contrast enhancement would have, in the example, a value of 2. Hence the vessel contrast in the image could be boosted with a factor of 2.

As a result, improved and stable contrast enhancement applied X-ray images can be achieved (e.g. optimized opacification and delineation in the anatomy, including lesions, can be achieved).

According to an example, the device further comprises an output unit. The output unit is configured to provide the dynamically contrast enhanced X-ray image. The output unit is, for example a display unit or monitor.

The output unit can also be referred to as an output interface, such as a graphical user output interface. In an example, the output unit transmits modified image data after applying the adapted image enhancement on the to be captured image.

According to a second aspect, an X-ray imaging system is provided. The X-ray imaging system comprises an X-ray imaging device, a contrast injection arrangement and a device for image contrast enhancement of an X-ray image of a vascular structure. The X-ray imaging device is configured to acquire the X-ray image of a vascular structure with a contrast injection. The contrast injection arrangement is adapted to perform the contrast injection with the current contrast injection setting having at least one contrast injection parameter.

In an example, the contrast injection arrangement can also be referred to as injector or contrast injector.

In an example, the contrast injection arrangement is configured to vary and/or adapt the current contrast injection setting. The contrast injection arrangement is configured to transmit the current contrast injection setting to the processing unit via the input interface. In an example, the data transmission can be a wireless connection to the processing unit or other type of data transmission (e.g. via cable connection).

According to an example, the contrast injection setting comprises a contrast injection parameter of at least one of the group of: delivered iodine concentration, injection timing, injection volume, injection speed, viscosity of iodine concentration, and injection real-time pressure curve.

The term "real-time pressure curve" relates to real-time concentration of iodine injected, i.e. the pressure with which the concentration is injected.

According to a third aspect, a method is provided for image contrast enhancement of an X-ray image of the vascular structure. The method comprises the following steps.

a) In a first step, an acquired X-ray image of a vascular structure with a contrast injection is provided. The contrast injection is performed with a current contrast injection setting having at least one contrast injection parameter.

b1) In a next step, a generic vascular structure is provided.

b2) In a further next step, the current injection setting is provided.

c) In another next step, assessed contrast distribution is determined for the generic vascular structure based on the current contrast injection setting.

d) In a next step, an adapted image contrast enhancement is determined for the generic vascular structure based on the assessed contrast distribution.

e) In a further next step, the adapted image contrast enhancement is applied to the acquired X-ray image of the patient's vascular structure in order to generate a contrast enhanced X-ray image.

In an example, in step d), the assessing of the contrast distribution is performed at least for a targeted vascular structure for which the image of the patient's vascular structure is captured.

In an example, steps a) to e) are arranged in a different order. For example, step b1) and/or b2) could be operated before step a).

According to an aspect, it is provided to enhance the image quality of an acquired X-ray image by adapting contrast boosting or contrast enhancement depending on the circumstances of the acquired image. As a result, the contrast enhancement is done dynamically. For example, when an image is captured for a thicker patient, the adapted contrast enhancement parameter is adapted to a higher level than for a thinner patient.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
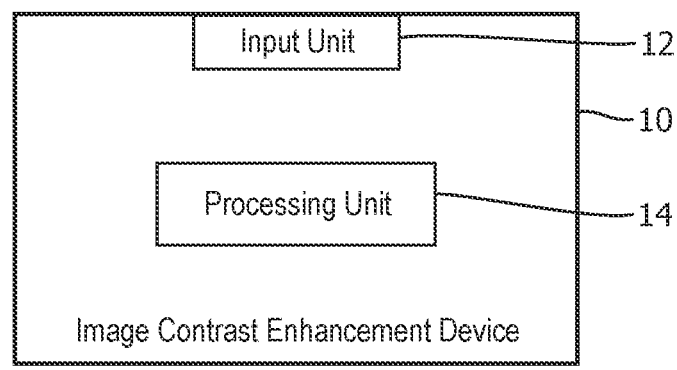
FIG. 1 shows an example of a device for image contrast enhancement of an X-ray image of a vascular structure.
Figure 2:
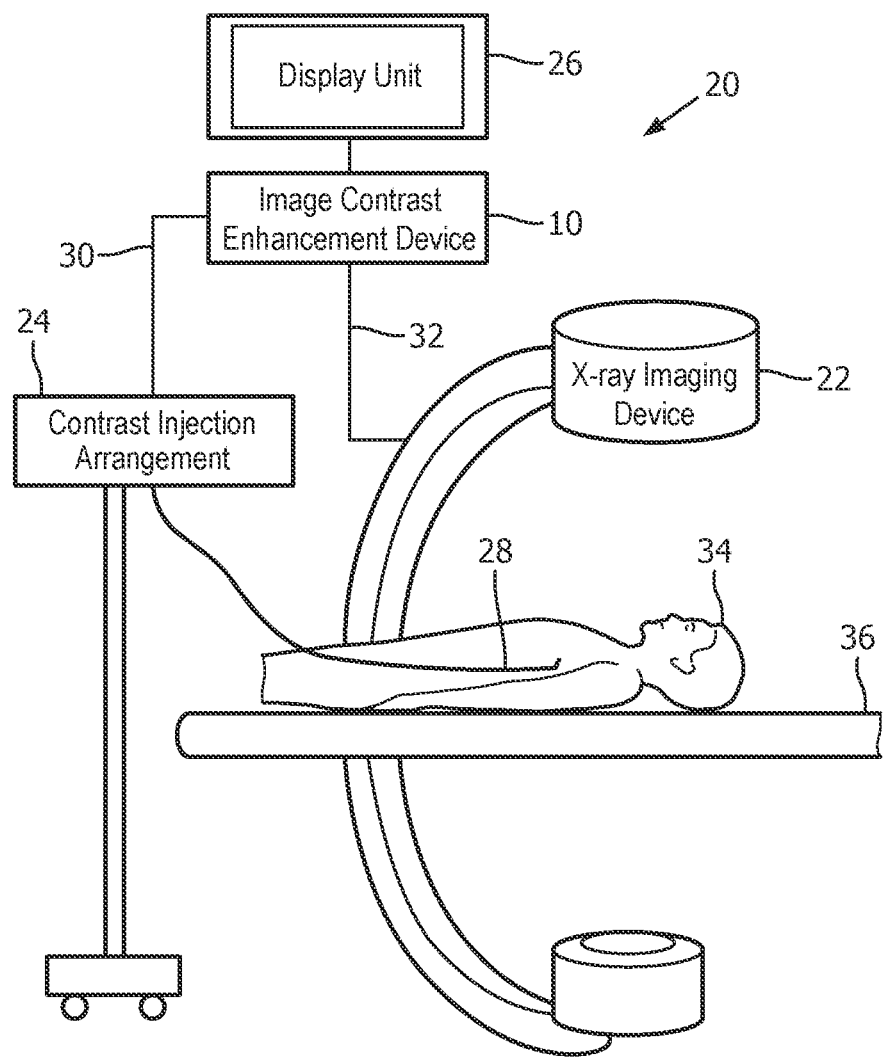
FIG. 2 shows an example of an X-ray imaging system with such a device.

FIG. 1 shows a device 10 for image contrast enhancement of an X-ray image of a vascular structure. The device 10 comprises an input unit 12 and a processing unit 14. The input unit 12 is configured to provide an acquired X-ray image of a vascular structure with a contrast injection (as shown in FIG. 2). The contrast injection is performed with a current contrast injection setting having at least one contrast injection parameter. The input unit 12 is configured to provide a generic vascular structure. The input unit 12 is also configured to provide the current contrast injection setting. The processing unit 14 is configured to determine an assessed contrast distribution for the generic vascular structure based on the current contrast injection setting. The processing unit 14 is also configured to determine an adapted image contrast enhancement for the generic vascular structure based on the assessed contrast distribution. The processing unit 14 is further configured to apply the adapted image contrast enhancement to the acquired X-ray image in order to generate a contrast-enhanced X-ray image.

In an example, an output unit (as shown in FIG. 2) is provided. The output unit is configured to provide the contrast enhanced X-ray image. In an example, the output unit is a display unit 26 for displaying the contrast enhanced X-ray image.

FIG. 2 shows an X-ray imaging system 20. The X-ray imaging system 20 comprises an X-ray imaging device 22, a contrast injection arrangement 24 and one of the examples of the device 10 for image contrast enhancement of an X-ray image of a vascular structure as described above and below. The X-ray imaging device is configured to acquire the X-ray image of a vascular structure with a contrast injection 28. The contrast injection arrangement is adapted to perform the contrast injection 28 with the current contrast injection setting having at least one contrast injection parameter.

In an example, the contrast injection arrangement 24 is adapted to perform the contrast injection 28 with the current contrast injection setting having at least one contrast injection parameter. In an example, the current contrast injection setting is transmitted to the device 10 (shown by connection line).

In an example, the acquired X-ray image is transmitted to the device 10, as shown by connection line 32.

FIG. 2 further shows a patient 34 lying on a table 36 during the acquisition of the X-ray image.

In an example, the acquisition of the X-ray image is operated in parallel to the injection of contrast dilution agent.

In an example, the current contrast injection setting is transmitted to the device in parallel to the acquisition of the X-ray image.

In another example, the current, i.e. applied contrast injection setting is transmitted after acquisition of the X-ray image.

In an example, the contrast injection arrangement 24 is movable.

In an example, the contrast injection setting comprises a contrast injection parameter of at least one of the group of: delivered iodine concentration, injection timing, injection volume, injection speed, viscosity of iodine concentration, and real-time pressure curve.

Figure 3:
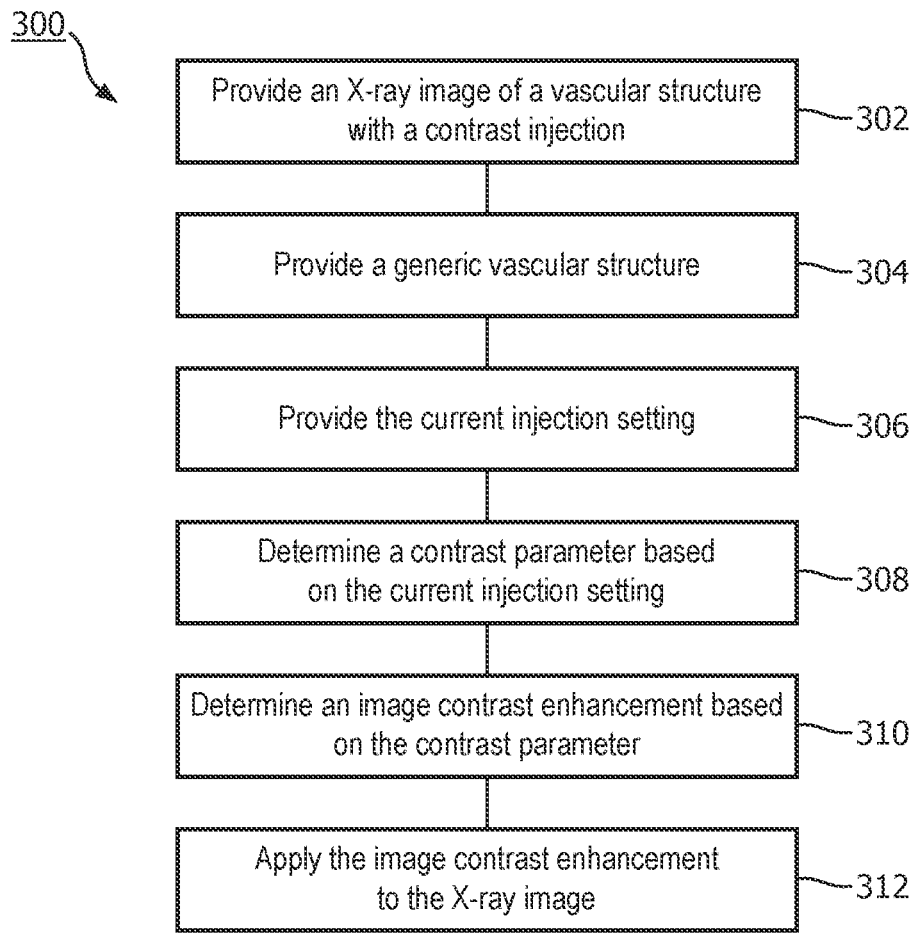
FIG. 3 illustrates an example of a method for image contrast enhancement of an X-ray image of a vascular structure.

FIG. 3 shows a method 300 for image contrast enhancement of an X-ray image of the vascular structure. The method comprises the following steps. In a first step 302, also referred to step as step a), an acquired X-ray image of a vascular structure with a contrast injection is provided. The contrast injection is performed with a current contrast injection setting having at least one contrast injection parameter. In a next step 304, also referred to as step b1), a generic vascular structure is provided. In a further next step 306, also referred to step b2), the current injection setting is provided. In a next step 308, also referred to step c), an assessed contrast distribution for the generic vascular structure based on the current contrast injection setting is determined. In a still next step 310, also referred to step d), an adapted image contrast enhancement for the generic vascular structure based on the assessed contrast distribution is determined. In a next step 312, also referred to step e), the adapted image contrast enhancement to the acquired X-ray image of the patient's vascular structure in order to generate a contrast enhanced X-ray image is applied.

In an example, for step 302 it is provided the step of acquiring the X-ray image of a vascular structure with a contrast injection, wherein the contrast injection is performed with the current contrast injection setting having at least one contrast injection parameter. In other words, the X-ray image is acquired at least almost in parallel to the transmission of the current injection setting.

In an example, the contrast injection setting comprises a contrast injection parameter of at least one of the group of: delivered iodine concentration, injection timing, injection volume, injection speed, viscosity of iodine concentration, and real-time pressure curve of at least one vessel of the vasculature structure.

In a not shown example, during step a) it is further provided the step of injecting contrast agent with a contrast injection setting. In a further not shown example, an adapted vascular structure is provided relating to a current specific vascular structure of a current patient in step b1. By providing a specific vascular structure of the patient the assessed contrast distribution can be determined even more precisely. In an example, the specific vascular structure can be obtained from previous measurements (e.g. other imaging procedures).

In a further not shown example, a contrast parameter of the assessed contrast distribution is determined. If the contrast parameter is below a pre-determined threshold, the adapted image contrast enhancement is determined and applied. If the contrast parameter is above the pre-determined threshold, the adaptive image contrast enhancement is not applied.

In an example, the threshold can be deduced or defined by previous measurements or investigations.

Figure 4:
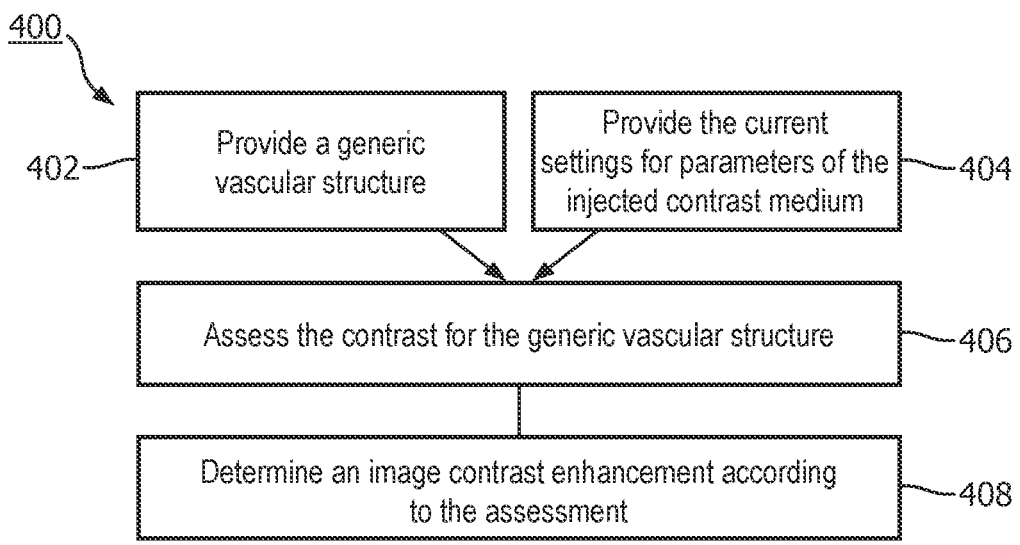
FIG. 4 illustrates another example of such a method.

FIG. 4 shows another exemplary embodiment of a method 400. In step 402 a generic vessel model of the targeted vascular structure is provided. In an example, a specific vessel model can be made as a refinement. The refinement may include a patient model. In step 404 the characteristics of the injected contrast medium, the so called current contrast injection parameters like dilution, volume speed, real-time pressure curve, viscosity, type of contrast medium, multi-head injector setting, or multi-syringe selection, are transmitted to the device. From step 402 and 404, one can deduce the contrast of those vessels prior boosting in step 406. In step 408, based on the estimation in step 406, the vessel contrast enhancement can be determined according the ambition. In other words, dynamic contrast enhancement is provided.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for image contrast enhancement of an X-ray image of a vascular structure, the device comprising:
   an input unit configured to:
      provide an acquired X-ray image of a vascular structure with a contrast injection, wherein the contrast injection is performed with a current contrast injection setting having at least one contrast injection parameter; and
      provide the current contrast injection setting; and
   a processor configured to:
      based on the current contrast injection setting, determine a prediction of an image contrast of at least a main vessel of the vascular structure;
      determine an adapted image contrast enhancement for the main vessel of the vascular structure based on the prediction of the image contrast, wherein the adapted image contrast enhancement defines an adaption to the acquired X-ray image to enhance the image contrast of the acquired X-ray image; and
      apply the adapted image contrast enhancement to the acquired X-ray image in order to generate a contrast enhanced X-ray image.

2. The device according to claim 1, further comprising an output unit configured to provide the contrast enhanced X-ray image; and
   wherein the output unit is a display.

3. An X-ray imaging system comprising:
   a device for image contrast enhancement of an X-ray image of a vascular structure according to claim 1;
   an X-ray imaging device configured to acquire the X-ray image of a vascular structure with a contrast injection; and
   a contrast injection arrangement configured to provide the contrast injection with the current contrast injection setting.

4. The system according to claim 3, wherein the contrast injection arrangement is configured to perform the contrast injection with the current contrast injection setting having at least one contrast injection parameter.

5. The system according to claim 3, wherein the contrast injection setting comprises a contrast injection parameter selected from the group consisting of: delivered iodine concentration, injection timing, injection volume, injection speed, viscosity of iodine concentration, and real-time pressure curve.

6. The device according to claim 1, wherein the processor is further configured to determine the prediction of the image contrast based on a specific condition of the patient.

7. The device according to claim 6, wherein the specific condition of the patient is selected from the group consisting of: specific vascular structure of the patient, anatomy of the patient, disease of the patient, and combinations thereof.

8. A method for image contrast enhancement of an X-ray image of a vascular structure, the method comprising:
   providing an acquired X-ray image of a vascular structure with a contrast injection, wherein the contrast injection is performed with a current contrast injection setting having at least one contrast injection parameter;
   based on the current contrast injection setting, determining a prediction of an image contrast of at least a main vessel of the vascular structure;
   determining an adapted image contrast enhancement for the main vessel of the vascular structure based on the prediction of the image contrast, wherein the adapted image contrast enhancement defines an adaption to the acquired X-ray image to enhance the image contrast of the acquired X-ray image; and
   applying the adapted image contrast enhancement to the acquired X-ray image of the patient's vascular structure in order to generate a contrast enhanced X-ray image.

9. The method according to claim 8, further comprising acquiring the X-ray image of a vascular structure with a contrast injection, wherein the contrast injection is performed with the current contrast injection setting having at least one contrast injection parameter.

10. The method according to claim 8, further comprising determining a current contrast parameter of the acquired X-ray image; and
wherein the adapted image contrast enhancement is applied if the current contrast parameter is below a pre-determined threshold.

11. The method according to claim 8, wherein the contrast injection setting comprises a contrast injection parameter selected from the group consisting of: delivered iodine concentration, injection timing, injection volume, injection speed, viscosity of iodine concentration, and real-time pressure curve of at least one vessel of the vasculature structure.

12. The method according to claim 8, further comprising: injecting contrast agent with a contrast injection setting.

13. The method according to claim 8, wherein the vascular structure comprises an adapted vascular structure relating to a current specific vascular structure of a current patient.

14. The method according to claim 8, wherein the prediction of the image contrast is determined based on a specific condition of the patient.

15. The method according to claim 14, wherein the specific condition of the patient is selected from the group consisting of: specific vascular structure of the patient, anatomy of the patient, disease of the patient, and combinations thereof.

16. A non-transitory computer-readable storage medium having stored thereon a computer program including instructions for controlling an X-ray imaging system, the instructions, when executed by a process, cause the processor to:
provide an acquired X-ray image of a vascular structure with a contrast injection, wherein the contrast injection is performed with a current contrast injection setting having at least one contrast injection parameter;
based on the current contrast injection setting, the assessed contrast parameter including determine a prediction of an image contrast of at least a main vessel of the vascular structure;
determine an adapted image contrast enhancement for the main vessel of the vascular structure based on the prediction of the image contrast, wherein the adapted image contrast enhancement defines an adaption to the acquired X-ray image to enhance the image contrast of the acquired X-ray image; and
apply the adapted image contrast enhancement to the acquired X-ray image of the patient's vascular structure in order to generate a contrast enhanced X-ray image.

17. The computer-readable storage medium according to claim 16, wherein the prediction of the image contrast is determined based on a specific condition of the patient.

18. The computer-readable storage medium according to claim 17, wherein the specific condition of the patient is selected from the group consisting of: specific vascular structure of the patient, anatomy of the patient, disease of the patient, and combinations thereof.

* * * * *